United States Patent
Song et al.

(10) Patent No.: US 7,179,919 B2
(45) Date of Patent: Feb. 20, 2007

(54) STEREOSELECTIVE SYNTHESIS OF CERTAIN TRIFLUOROMETHYL-SUBSTITUTED ALCOHOLS

(75) Inventors: Jinhua J. Song, Hopewell Junction, NY (US); Zhulin Tan, Danbury, CT (US); Nathan K. Yee, Danbury, CT (US); Chris Hugh Senanayake, Brookfield, CT (US); Jinghua Xu, Bethel, CT (US); Fabrice Gallou, Danbury, CT (US)

(73) Assignee: Boehringer Ingelheim Pharmaceuticals, Inc., Ridgefield, CT (US)

( * ) Notice: Subject to any disclaimer, the term of this patent is extended or adjusted under 35 U.S.C. 154(b) by 88 days.

(21) Appl. No.: 11/070,462

(22) Filed: Mar. 2, 2005

(65) Prior Publication Data

US 2005/0209488 A1    Sep. 22, 2005

Related U.S. Application Data

(60) Provisional application No. 60/554,266, filed on Mar. 18, 2004.

(51) Int. Cl.
*C07D 471/04*    (2006.01)

(52) U.S. Cl. .................................................. 546/113
(58) Field of Classification Search .................. 546/113
See application file for complete search history.

(56) References Cited

FOREIGN PATENT DOCUMENTS

WO    WO 03/082280 A1    10/2003

OTHER PUBLICATIONS

Hong, H. et al ; Synthesis and Protein Kinase C Inhibitory Activities of Indane Analongs of Balanol, Bioorganic & Medicinal Chemistry Letters, vol. 6, No. 8, pp. 973-978, 1996.

*Primary Examiner*—Joseph K. McKane
*Assistant Examiner*—Jason M. Nolan
(74) *Attorney, Agent, or Firm*—Michael P. Morris; Timothy X. Witkowski; Mary-Ellen Devlin

(57) ABSTRACT

A process for stereoselective synthesis of a compound of Formula (I)

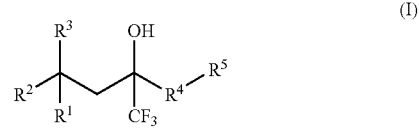

wherein $R^1$, $R^2$, $R^3$, $R^4$, and $R^5$ are as described herein.

19 Claims, No Drawings

STEREOSELECTIVE SYNTHESIS OF CERTAIN TRIFLUOROMETHYL-SUBSTITUTED ALCOHOLS

RELATED APPLICATIONS

This application claims benefit of U.S. Ser. No. 60/554,266, filed Mar. 18, 2004, which is hereby incorporated by reference in its entirety.

FIELD OF THE INVENTION

The present invention relates to the stereoselective synthesis of certain trifluoromethyl-substituted alcohols.

BACKGROUND OF THE INVENTION

Trifluoromethyl-substituted alcohols of formula (I) have been described as ligands that bind to the glucocorticoid receptor. These compounds are effective as therapeutics in treating a number of diseases modulated by glucocorticoid receptor function, including inflammatory, autoimmune and allergic disorders. Examples of these compounds are described in U.S. Patent Application Publication Nos. 2003/0232823, 2004/0029932, and 2004/0023999, which are each incorporated herein by reference in their entireties and are hereinafter termed "the Trifluoromethyl-Substituted Alcohol Patent Applications".

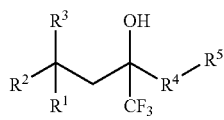
(I)

It is well known in the art that enantiomers of a particular compound can have different biological properties including efficacy, toxicity, and pharmacokinetic properties. Thus, it is often desirable to administer one enantiomer of a racemic therapeutic compound.

The synthetic methods disclosed in the patent applications cited above describe the synthesis of racemic products. Separation of enantiomers was accomplished by chiral HPLC and may be accomplished by other conventional ways of separating enantiomers. Chiral HPLC and other enantiomer separation method, however, are generally unsuitable for large-scale preparation of a single enantiomer. Thus, a stereoselective synthesis for preparation of these compounds would be highly desirable.

The present invention discloses a stereoselective synthesis of certain compounds of formula (I). A key step involves a novel ester to azaindole reaction. There are no examples of a direct azaindole formation from ester groups in the chemical literature.

SUMMARY OF THE INVENTION

The instant invention is directed to a process for stereoselective synthesis of a compound of Formula (I)

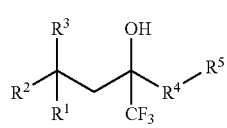
(I)

wherein:
$R^1$ is an aryl or heteroaryl group, each optionally substituted with one to three substituent groups,
wherein each substituent group of $R^1$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, $C_1$-$C_5$ alkanoyloxy, $C_1$-$C_5$ alkanoyl, aroyl, trifluoromethyl, trifluoromethoxy, or $C_1$-$C_5$ alkylthio,
wherein each substituent group of $R^1$ is optionally independently substituted with one to three substituent groups selected from methyl, methoxy, fluoro, chloro, or alkoxy;
$R^2$ and $R^3$ are each independently hydrogen or $C_1$-$C_5$ alkyl, or $R^2$ and $R^3$ together with the carbon atom they are commonly attached to form a $C_3$-$C_8$ spiro cycloalkyl ring;
$R^4$ is $C_1$-$C_5$ alkyl, $C_2$-$C_5$ alkenyl, or $C_2$-$C_5$ alkynyl, each optionally substituted with one to three substituent groups,
wherein each substituent group of $R^4$ is independently $C_1$-$C_3$ alkyl, hydroxy, halogen, amino, or oxo; and
$R^5$ is the moiety

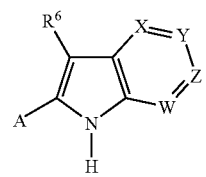

wherein A is the point of attachment to $R^4$, W, X, Y, or Z is N or CH and at least one of W, X, Y, or Z is N, $R^6$ is H, alkyl, or aryl, and $R^5$ is optionally substituted with one to three substituent groups,
wherein each substituent group of $R^5$ is independently $C_1$-$C_5$ alkyl, $C_2$-$C_5$ alkenyl, $C_2$-$C_5$ alkynyl, $C_3$-$C_8$ cycloalkyl, heterocyclyl, aryl, heteroaryl, $C_1$-$C_5$ alkoxy, $C_2$-$C_5$ alkenyloxy, $C_2$-$C_5$ alkynyloxy, aryloxy, acyl, $C_1$-$C_5$ alkoxycarbonyl, $C_1$-$C_5$ alkanoyloxy, aminocarbonyl, alkylaminocarbonyl, dialkylaminocarbonyl, aminocarbonyloxy, $C_1$-$C_5$ alkylaminocarbonyloxy, $C_1$-$C_5$ dialkylaminocarbonyloxy, $C_1$-$C_5$ alkanoylamino, $C_1$-$C_5$ alkoxycarbonylamino, $C_1$-$C_5$ alkylsulfonylamino, aminosulfonyl, $C_1$-$C_5$ alkylaminosulfonyl, $C_1$-$C_5$ dialkylaminosulfonyl, halogen, hydroxy, carboxy, cyano, trifluoromethyl, trifluoromethoxy, trifluoromethylthio, nitro, or amino wherein the nitrogen atom is optionally independently mono- or di-substituted by $C_1$-$C_5$ alkyl; or ureido wherein either nitrogen atom is optionally independently substituted with $C_1$-$C_5$ alkyl; or $C_1$-$C_5$ alkylthio wherein the sulfur atom is optionally oxidized to a sulfoxide or sulfone,
wherein each substituent group of $R^5$ is optionally independently substituted with one to three substituent groups selected from $C_1$–$C_3$ alkyl, $C_1$–$C_3$ alkoxy, halogen, hydroxy, oxo, cyano, amino, or trifluoromethyl, the process comprising:

(a) reacting a starting material of formula A with a first protecting group agent PG-Y, where Y is a leaving group, in a suitable solvent, followed by addition of an acetylating reagent and a suitable base to prepare a protected intermediate of formula B

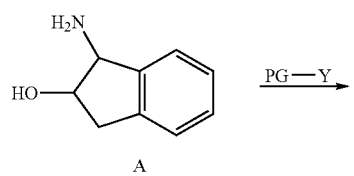

A

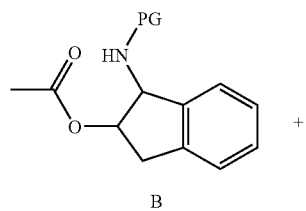

B (b) reacting the protected intermediate of formula B with a trifluoromethyl-substituted ketone of formula C in the presence of a suitable base in a suitable solvent to obtain a compound of formula D

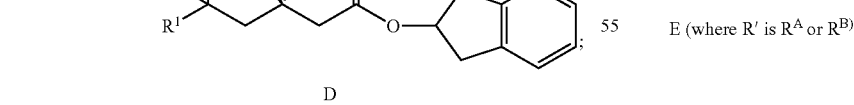

(c) reacting the compound of formula D with a suitable metal alkoxide, $(R^A$—$O)_\mu M$, where $R^A$ is an alkyl or aryl group, M is a suitable metal atom, and $\mu$ is an integer number, in a suitable solvent followed by reaction of the tertiary alcohol with a second protecting group agent PG'-Y', where Y' is a leaving group, to obtain the ester of formula E

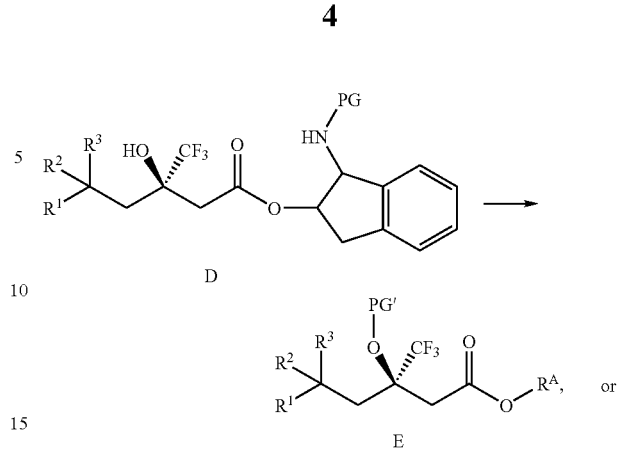

(c') hydrolyzing the compound of formula D followed by esterification of the free acid with a suitable alcohol, $R^B$—OH, where $R^B$ is an alkyl or aryl group, and protection of the tertiary alcohol as in (c) to provide the ester of formula E (d) reacting the ester of formula E with a compound of formula F, wherein W, X, Y, or Z is N or CH, at least one of W, X, Y, or Z is N, and $R^6$ is H, alkyl, or aryl, in the presence of a suitable base, in a suitable solvent to obtain a compound of formula G In an aspect of the invention, the suitable solvent of step (a) is dimethyl ether, diethyl ether, dipropyl ether, diisopropyl ether, dibutyl ether, tetrahydrofuran (THF), ethylene glycol dimethyl ether (DME), tert-butyl methyl ether (MTBE), or a mixture thereof, preferably tetrahydrofuran. In another aspect of the invention, the suitable base for step (a) is selected from trialkylamines such as triethyl amine (TEA) and diisopropylethyl amine, pyridine bases such as pyridine and 4-dimethylaminopyridine (DMAP), and inorganic bases such as $Na_2CO_3$ and NaOH, preferably TEA. In another aspect of the invention, in the first protecting group agent PG-Y of step (a), the first protecting group PG is selected from aryl or alkyl sulfonyl groups such as tosyl or mesyl, mesityl, preferably tosyl and the first leaving group Y is selected from Cl, Br, I, MsO, TsO, and TfO, preferably Cl. In another aspect of the invention, the suitable acetylating reagent for step (a) is acetic anhydride or acetyl chloride, preferably acetic anhydride.

In another aspect of the invention, the suitable solvent of step (b) is diethyl ether, dipropyl ether, diisopropyl ether, dibutyl ether, tetrahydrofuran (THF), ethylene glycol dimethyl ether (DME), tert-butyl methyl ether (MTBE), toluene, hexane, heptane, or a mixture thereof, preferably tetrahydrofuran. In another aspect of the invention, the suitable base for step (b) is lithium hexamethyldisilazide (LiHMDS), sodium hexamethyldisilazide (NaHMDS), potassium hexamethyldisilazide (KHMDS), LDA, LiH, NaH, KH, trialkylamine/$R_2$BOTf (dialkylboryl trifluoromethanesulfonate), trialkylamine/$TiCl_4$, or trialkylamine/$TiCl_2(OiPr)_2$, optionally including additives such as sparteine, $MgBr_2$, $TiC_4$, or $ZnCl_2$, preferably LiHMDS.

In yet another aspect of the invention, the M of the suitable metal alkoxide of step (c) is lithium, sodium, potassium, rubidium, or cesium, and μ is 1. In another aspect of the invention, the M of the suitable metal alkoxide of step (c) is selected from magnesium, calcium, or barium, and μ is 2. In another aspect of the invention, $R^A$ of the suitable metal alkoxide of step (c) is an alkyl or aryl group. In another aspect of the invention, the suitable metal alkoxide of step (c) is an alkali metal alkoxide, preferably sodium methoxide. In another aspect of the invention, the suitable solvent of step (c) is tetrahydrofuran (THF), methanol, ethanol, water, DME, MTBE, isopropyl alcohol (IPA), dimethyl ether, dipropyl ether, diisopropyl ether, or a mixture thereof, preferably methanol.

In another aspect of the invention, the hydrolysis of step (c') is accomplished with an alkali metal hydroxide, phase transfer hydrolysis, or acid hydrolysis in a suitable solvent selected from tetrahydrofuran (THF), methanol, ethanol, water, DME, MTBE, IPA, dimethyl ether, dipropyl ether, diisopropyl ether, or a mixture thereof, preferably MeOH. In another aspect of the invention, the esterification of step (c') is carried out by treatment of the free acid with methanol in the presence of an acid catalyst. In another aspect of the invention, in the second protecting group agent PG'-Y' of step (c) or (c'), the second protecting group PG' is a trialkylsilyl group, lower alkyl ether (e.g., methoxymethyl ether (MOM ether)), lower alkyl group, or internally protected as β-lactone with the terminal carboxyl group, and the second leaving group Y' is Cl, Br, I, MsO, TsO, and TfO, preferably Cl.

In another aspect of the invention, the suitable solvent of step (d) is THF, DME, diethyl ether, dipropyl ether, diisopropyl ether, dibutyl ether, MTBE, toluene, benzene, xylene, hexane, pentane, heptane, methylene chloride, or a mixture thereof, and is preferably THF. In another aspect of the invention, the suitable base of step (d) is n-BuLi, sec-BuLi, or tert-BuLi, optionally including additives such as N,N,N', N'-tetramethylethylenediamine (TMEDA), β-dialkylaminoalcohols, sparteine, or polyethers, preferably sec-BuLi.

In another aspect of the invention, the compound of formula F is 3-amino-4-picoline, 4-amino-3-picoline, 2-amino-3-picoline, or 3-amino-2-picoline, each optionally substituted on the ring or methyl group with a substituent compatible with alkyl lithium, preferably 3-amino-4-picoline.

While certain specific embodiments of the invention, including specific reaction conditions, solvents, protecting groups, and other reagents and reactants are described above in detailing various aspects of the invention, it should be understood that no particular limitation to these specific embodiments or aspects should limit the invention in its broadest sense. Accordingly, the invention should be understood to include none, some, or all of these various aspects in various combinations.

DETAILED DESCRIPTION OF THE INVENTION

Definition of Terms and Conventions Used

Terms not specifically defined herein should be given the meanings that would be given to them by one of skill in the art in light of the disclosure and the context. As used in the specification and appended claims, however, unless specified to the contrary, the following terms have the meaning indicated and the following conventions are adhered to.

A. Chemical Nomenclature, Terms, and Conventions

In the groups, radicals, or moieties defined below, the number of carbon atoms is often specified preceding the group, for example, $C_1-C_{10}$ alkyl means an alkyl group or radical having 1 to 10 carbon atoms. The term "lower" applied to any carbon-containing group means a group containing from 1 to 8 carbon atoms, as appropriate to the group (i.e., a cyclic group must have at least 3 atoms to constitute a ring). In general, for groups comprising two or more subgroups, the last named group is the radical attachment point, for example, "alkylaryl" means a monovalent radical of the formula Alk-Ar-, while "arylalkyl" means a monovalent radical of the formula Ar-Alk- (where Alk is an alkyl group and Ar is an aryl group). Furthermore, the use of a term designating a monovalent radical where a divalent radical is appropriate shall be construed to designate the respective divalent radical and vice versa. Unless otherwise specified, conventional definitions of terms control and conventional stable atom valences are presumed and achieved in all formulas and groups.

The terms "alkyl" or "alkyl group" mean a branched or straight-chain saturated aliphatic hydrocarbon monovalent radical. This term is exemplified by groups such as methyl, ethyl, n-propyl, 1-methylethyl (isopropyl), n-butyl, n-pentyl, 1,1-dimethylethyl (tert-butyl), and the like. It may be abbreviated "Alk".

The terms "alkenyl" or "alkenyl group" mean a branched or straight-chain aliphatic hydrocarbon monovalent radical containing at least one carbon-carbon double bond. This term is exemplified by groups such as ethenyl, propenyl, n-butenyl, isobutenyl, 3-methylbut-2-enyl, n-pentenyl, heptenyl, octenyl, decenyl, and the like.

The terms "alkynyl" or "alkynyl group" mean a branched or straight-chain aliphatic hydrocarbon monovalent radical containing at least one carbon-carbon triple bond. This term is exemplified by groups such as ethynyl, propynyl, n-butynyl, 2-butynyl, 3-methylbutynyl, n-pentynyl, heptynyl, octynyl, decynyl, and the like.

The terms "alkylene" or "alkylene group" mean a branched or straight-chain saturated aliphatic hydrocarbon divalent radical having the specified number of carbon atoms. This term is exemplified by groups such as methylene, ethylene, propylene, n-butylene, and the like, and may alternatively and equivalently be denoted herein as -(alkyl)-.

The terms "alkenylene" or "alkenylene group" mean a branched or straight-chain aliphatic hydrocarbon divalent radical having the specified number of carbon atoms and at least one carbon-carbon double bond. This term is exemplified by groups such as ethenylene, propenylene, n-butenylene, and the like, and may alternatively and equivalently be denoted herein as -(alkylenyl)-.

The terms "alkynylene" or "alkynylene group" mean a branched or straight-chain aliphatic hydrocarbon divalent radical containing at least one carbon-carbon triple bond. This term is exemplified by groups such as ethynylene, propynylene, n-butynylene, 2-butynylene, 3-methylbutynylene, n-pentynylene, heptynylene, octynylene, decynylene, and the like, and may alternatively and equivalently be denoted herein as -(alkynyl)-.

The terms "alkoxy" or "alkoxy group" mean a monovalent radical of the formula AlkO-, where Alk is an alkyl group. This term is exemplified by groups such as methoxy, ethoxy, propoxy, isopropoxy, butoxy, sec-butoxy, tert-butoxy, pentoxy, and the like.

The terms "aryloxy", "aryloxy group", mean a monovalent radical of the formula ArO-, where Ar is aryl. This term is exemplified by groups such as phenoxy, naphthoxy, and the like.

The terms "alkylcarbonyl", "alkylcarbonyl group", "alkanoyl", or "alkanoyl group" mean a monovalent radical of the formula AlkC(O)-, where Alk is alkyl or hydrogen.

The terms "arylcarbonyl", "arylcarbonyl group", "aroyl" or "aroyl group" mean a monovalent radical of the formula ArC(O)-, where Ar is aryl.

The terms "acyl" or "acyl group" mean a monovalent radical of the formula RC(O)—, where R is a substituent selected from hydrogen or an organic substituent. Exemplary substituents include alkyl, aryl, arylalkyl, cycloalkyl, heterocyclyl, heteroaryl, heteroarylalkyl, and the like. As such, the terms comprise alkylcarbonyl groups and arylcarbonyl groups.

The terms "acylamino" or "acylamino group" mean a monovalent radical of the formula RC(O)N(R)—, where each R is a substituent selected from hydrogen or a substituent group.

The terms "alkoxycarbonyl" or "alkoxycarbonyl group" mean a monovalent radical of the formula AlkO-C(O)—, where Alk is alkyl. Exemplary alkoxycarbonyl groups include methoxycarbonyl, ethoxycarbonyl, tert-butyloxycarbonyl, and the like.

The terms "alkylaminocarbonyloxy" or "alkylaminocarbonyloxy group" mean a monovalent radical of the formula $R_2NC(O)O$—, where each R is independently hydrogen or lower alkyl.

The term "alkoxycarbonylamino" or "alkoxycarbonylamino group" mean a monovalent radical of the formula ROC(O)NH—, where R is lower alkyl.

The terms "alkylcarbonylamino" or "alkylcarbonylamino group" or "alkanoylamino" or "alkanoylamino groups" mean a monovalent radical of the formula AlkC(O)NH—, where Alk is alkyl. Exemplary alkylcarbonylamino groups include acetamido ($CH_3C(O)NH$—).

The terms "alkylaminocarbonyloxy" or "alkylaminocarbonyloxy group" mean a monovalent radical of the formula AlkNHC(O)O—, where Alk is alkyl.

The terms "amino" or "amino group" mean an —$NH_2$ group.

The terms "alkylamino" or "alkylamino group" mean a monovalent radical of the formula (Alk)NH—, where Alk is alkyl. Exemplary alkylamino groups include methylamino, ethylamino, propylamino, butylamino, tert-butylamino, and the like.

The terms "dialkylamino" or "dialkylamino group" mean a monovalent radical of the formula (Alk)(Alk)N—, where each Alk is independently alkyl. Exemplary dialkylamino groups include dimethylamino, methylethylamino, diethylamino, dipropylamino, ethylpropylamino, and the like.

The terms "substituted amino" or "substituted amino group" mean a monovalent radical of the formula —$NR_2$, where each R is independently a substituent selected from hydrogen or the specified substituents (but where both Rs cannot be hydrogen). Exemplary substituents include alkyl, alkanoyl, aryl, arylalkyl, cycloalkyl, heterocyclyl, heteroaryl, heteroarylalkyl, and the like.

The terms "alkoxycarbonylamino" or "alkoxycarbonylamino group" mean a monovalent radical of the formula AlkOC(O)NH—, where Alk is alkyl.

The terms "ureido" or "ureido group" mean a monovalent radical of the formula $R_2NC(O)NH$—, where each R is independently hydrogen or alkyl.

The terms "halogen" or "halogen group" mean a fluoro, chloro, bromo, or iodo group.

The term "halo" means one or more hydrogen atoms of the group are replaced by halogen groups.

The terms "alkylthio" or "alkylthio group" mean a monovalent radical of the formula AlkS-, where Alk is alkyl. Exemplary groups include methylthio, ethylthio, n-propylthio, isopropylthio, n-butylthio, and the like.

The terms "sulfonyl" or "sulfonyl group" mean a divalent radical of the formula —$SO_2$—.

The terms "carbocycle" or "carbocyclic group" mean a stable aliphatic 3- to 15-membered monocyclic or polycyclic monovalent or divalent radical consisting solely of carbon and hydrogen atoms which may comprise one or more fused or bridged ring(s), preferably a 5- to 7-membered monocyclic or 7- to 10-membered bicyclic ring. Unless otherwise specified, the carbocycle may be attached at any carbon atom which results in a stable structure and, if substituted, may be substituted at any suitable carbon atom which results in a stable structure. The term comprises cycloalkyl (including spiro cycloalkyl), cycloalkylene, cycloalkenyl, cycloalkenylene, cycloalkynyl, and cycloalkynylene, and the like. The terms "cycloalkyl" or "cycloalkyl group" mean a stable aliphatic saturated 3- to 15-membered monocyclic or polycyclic monovalent radical consisting solely of carbon and hydrogen atoms which may comprise one or more fused or bridged ring(s), preferably a 5- to 7-membered monocyclic or 7- to 10-membered bicyclic ring. Unless otherwise specified, the cycloalkyl ring may be attached at any carbon atom which results in a stable structure and, if substituted, may be substituted at any suitable carbon atom which results in a stable structure. Exemplary cycloalkyl groups include cyclopropyl, cyclobutyl, cyclopentyl, cyclohexyl, cycloheptyl, cyclooctyl, cyclononyl, cyclodecyl, norbornanyl, adamantyl, tetrahydronaphthyl (tetralin), 1-decalinyl, bicyclo[2.2.2] octanyl, 1-methylcyclopropyl, 2-methylcyclopentyl, 2-methylcyclooctyl, and the like.

The terms "aryl" or "aryl group" mean an aromatic carbocyclic monovalent or divalent radical of from 6 to 14 carbon atoms having a single ring (e.g., phenyl or phenylene) or multiple condensed rings (e.g., naphthyl or anthranyl). Unless otherwise specified, the aryl ring may be attached at any suitable carbon atom which results in a stable structure and, if substituted, may be substituted at any suitable carbon atom which results in a stable structure.

Exemplary aryl groups include phenyl, naphthyl, anthryl, phenanthryl, indanyl, indenyl, biphenyl, and the like. It may be abbreviated "Ar".

The terms "heteroaryl" or "heteroaryl group" mean a stable aromatic 5- to 14-membered, monocyclic or polycyclic monovalent or divalent radical which may comprise one or more fused or bridged ring(s), preferably a 5- to 7-membered monocyclic or 7- to 10-membered bicyclic radical, having from one to four heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heteroaryl ring may be attached at any suitable heteroatom or carbon atom which results in a stable structure and, if substituted, may be substituted at any suitable heteroatom or carbon atom which results in a stable structure. Exemplary and preferred heteroaryls include furanyl, thienyl, pyrrolyl, oxazolyl, thiazolyl, imidazolyl, pyrazolyl, isoxazolyl, isothiazolyl, oxadiazolyl, triazolyl, tetrazolyl, thiadiazolyl, pyridinyl, pyridazinyl, pyrimidinyl, pyrazinyl, triazinyl, indolizinyl, azaindolizinyl, indolyl, azaindolyl, diazaindolyl, dihydroindolyl, dihydroazaindoyl, isoindolyl, azaisoindolyl, benzofuranyl, furanopyridinyl, furanopyrimidinyl, furanopyrazinyl, furanopyridazinyl, dihydrobenzofuranyl, dihydrofuranopyridinyl, dihydrofuranopyrimidinyl, benzodioxolanyl, benzothienyl, thienopyridinyl, thienopyrimidinyl, thienopyrazinyl, thienopyridazinyl, dihydrobenzothienyl, dihydrothienopyridinyl, dihydrothienopyrimidinyl, indazolyl, azaindazolyl, diazaindazolyl, benzimidazolyl, imidazopyridinyl, benzthiazolyl, thiazolopyridinyl, thiazolopyrimidinyl, benzoxazolyl, oxazolopyridinyl, oxazolopyrimidinyl, benzisoxazolyl, purinyl, chromanyl, azachromanyl, quinolizinyl, quinolinyl, dihydroquinolinyl, tetrahydroquinolinyl, isoquinolinyl, dihydroisoquinolinyl, tetrahydroisoquinolinyl, cinnolinyl, azacinnolinyl, phthalazinyl, azaphthalazinyl, quinazolinyl, azaquinazolinyl, quinoxalinyl, azaquinoxalinyl, naphthyridinyl, dihydronaphthyridinyl, tetrahydronaphthyridinyl, pteridinyl, carbazolyl, acridinyl, phenazinyl, phenothiazinyl, and phenoxazinyl, and the like.

The terms "heterocycle", "heterocycle group", "heterocyclyl", or "heterocyclyl group" mean a stable non-aromatic 5- to 14-membered monocyclic or polycyclic, monovalent or divalent, ring which may comprise one or more fused or bridged ring(s), preferably a 5- to 7-membered monocyclic or 7- to 10-membered bicyclic ring, having from one to three heteroatoms in the ring(s) independently selected from nitrogen, oxygen, and sulfur, wherein any sulfur heteroatoms may optionally be oxidized and any nitrogen heteroatom may optionally be oxidized or be quaternized. Unless otherwise specified, the heterocyclyl ring may be attached at any suitable heteroatom or carbon atom which results in a stable structure and, if substituted, may be substituted at any suitable heteroatom or carbon atom which results in a stable structure. Exemplary and preferred heterocycles include pyrrolinyl, pyrrolidinyl, pyrazolinyl, pyrazolidinyl, piperidinyl, morpholinyl, thiomorpholinyl, piperazinyl, tetrahydropyranyl, tetrahydrothiopyranyl, tetrahydrofuranyl, hexahydropyrimidinyl, hexahydropyridazinyl, and the like.

The term "compounds of the invention" and equivalent expressions are meant to embrace compounds of Formula (I) as herein described, including the tautomers, the prodrugs, the salts, particularly the pharmaceutically acceptable salts, and the solvates and hydrates thereof, where the context so permits. In general and preferably, the compounds of the invention and the formulas designating the compounds of the invention are understood to only include the stable compounds thereof and exclude unstable compounds, even if an unstable compound might be considered to be literally embraced by the compound formula. Similarly, reference to intermediates, whether or not they themselves are claimed, is meant to embrace their salts and solvates, where the context so permits. For the sake of clarity, particular instances when the context so permits are sometimes indicated in the text, but these instances are purely illustrative and it is not intended to exclude other instances when the context so permits.

The term "leaving group" means a group with the meaning conventionally associated with it in synthetic organic chemistry, that is, an atom or group displaceable under substitution reaction conditions. Examples of leaving groups include, but are not limited to, halogen, alkane- or arylenesulfonyloxy, such as methanesulfonyloxy, ethanesulfonyloxy, thiomethyl, benzenesulfonyloxy, tosyloxy, and thienyloxy, dihalophosphinoyloxy, optionally substituted benzyloxy, isopropyloxy, acyloxy, and the like.

The term "solvent" or "suitable solvent" means a solvent or a mixture of solvents that is substantially inert under the conditions of the reaction being described in conjunction therewith, including, for example, dimethyl ether, diethyl ether, dipropyl ether, diisopropyl ether, dibutyl ether, tetrahydrofuran (THF), ethylene glycol dimethyl ether (DME), tert-butyl methyl ether (MTBE), benzene, toluene, acetonitrile, N,N-dimethylformamide, chloroform, methylene chloride, dichloroethane, ethyl acetate, acetone, methyl ethyl ketone, methanol, ethanol, propanol, isopropanol, tert-butanol, dioxane, pyridine, and the like, or mixtures thereof. Unless specified to the contrary, the solvents used in the reactions of the present invention are substantially inert solvents.

The term "protecting group" means a chemical group which selectively blocks one reactive site in a multifunctional compound such that a chemical reaction can be carried out selectively at another unprotected reactive site in the meaning conventionally associated with it in synthetic chemistry. Certain synthetic steps of the invention rely upon the protective groups to block reactive atoms, for example, nitrogen or hydrogen atoms, present in the reactants. For example, an amino protecting group or nitrogen protecting group is an organic group intended to protect the nitrogen atom against undesirable reactions during synthetic procedures. Exemplary nitrogen protecting groups include, but are not limited to, trifluoroacetyl, acetamido, benzyl (Bn), benzyloxycarbonyl (carbobenzyloxy, CBZ), p-methoxybenzyloxycarbonyl, p-nitrobenzyloxycarbonyl, tert-butoxycarbonyl (BOC), and the like. Similarly, a hydroxy protecting group is an organic group intended to protect the oxygen atom of a hydroxyl group against undesirable reactions during synthetic procedures. Exemplary hydroxy protecting groups include, but are not limited to benzyl, silyl groups, tetrahydropyranyl, esters, and the like. One of skill in the art, based on the instant specification, will know how to chose a suitable protecting group for the ease of removal and for the ability to withstand the subsequent reactions. Certain protecting groups are described, for example, in J. F. W. McOmie (ed.), *Protective Groups in Organic Chemistry*, Plenum Press, 1973; T. W. Greene & P. G. M. Wuts, *Protective Groups in Organic Synthesis* (3rd Ed.), John Wiley & Sons, 1999; and P. J. Kocienski, *Protecting Groups* ($2^{nd}$ Ed.) Theime Medical Pub., 2000, each of which is incorporated by reference in its entirety. Protecting groups may be removed at a convenient subsequent stage using methods known in the art or by metabolic or other in vivo administration conditions.

The term "protecting group agent" means reaction conditions or a reagent that supplies a desired protecting group to the substrate.

The terms "optional" or "optionally" mean that the subsequently described event or circumstances may or may not occur, and that the description includes instances where the event or circumstance occurs and instances in which it does not. For example, "optionally substituted aryl" means that the aryl radical may or may not be substituted and that the description includes both substituted aryl radicals and aryl radicals having no substitution.

The terms "stable compound" or "stable structure" mean a compound that is sufficiently robust to survive isolation to a useful degree of purity from a reaction mixture, and formulation into an efficacious therapeutic or diagnostic agent. For example, a compound which would have a "dangling valency" or is a carbanion is not a compound contemplated by the invention.

The term "substituted" means that any one or more hydrogens on an atom of a group or moiety, whether specifically designated or not, is replaced with a selection from the indicated group of substituents, provided that the atom's normal valency is not exceeded and that the substitution results in a stable compound. If a bond to a substituent is shown to cross the bond connecting two atoms in a ring, then such substituent may be bonded to any atom on the ring. When a substituent is listed without indicating the atom via which such substituent is bonded to the rest of the compound, then such substituent may be bonded via any atom in such substituent. For example, when the substituent is piperazinyl, piperidinyl, or tetrazolyl, unless specified otherwise, such piperazinyl, piperidinyl, or tetrazolyl group may be bonded to the rest of the compound of the invention via any atom in such piperazinyl, piperidinyl, or tetrazolyl group. Generally, when any substituent or group occurs more than one time in any constituent or compound, its definition on each occurrence is independent of its definition at every other occurrence. Thus, for example, if a group is shown to be substituted with 0 to 2 $R^5$, then such group is optionally substituted with up to two $R^5$ groups and $R^5$ at each occurrence is selected independently from the defined list of possible $R^5$. Such combinations of substituents and/or variables, however, are permissible only if such combinations result in stable compounds.

In a specific embodiment, the term "about" or "approximately" means within 20%, preferably within 10%, and more preferably within 5% of a given value or range.

The yield of each of the reactions described herein is expressed as a percentage of the theoretical yield.

EXPERIMENTAL EXAMPLES

The invention provides processes for making compounds of Formula (I). In all schemes, unless specified otherwise, $R^1$ to $R^5$ in the formulas below can have the meanings of $R^1$ to $R^5$ set forth herein and additionally in the Trifluoromethyl-Substituted Alcohol Patent Applications. Intermediates used in the preparation of compounds of the invention are either commercially available or readily prepared by methods known to those skilled in the art.

Optimum reaction conditions and reaction times may vary depending on the particular reactants used. Unless otherwise specified, solvents, temperatures, pressures, and other reaction conditions may be readily selected by one of ordinary skill in the art. Specific procedures are provided in the Experimental Examples section. Typically, reaction progress may be monitored by high performance liquid chromatography (HPLC) or thin layer chromatography (TLC), if desired, and intermediates and products may be purified by chromatography on silica gel and/or by recrystallization.

SYNTHETIC EXAMPLE

The following is a representative example that illustrates the process of the invention. HPLC used to characterize products and intermediates were done on a $C_{18}$ Super-ODS column (Supelco, part no. 818197, 4.6 mm×10 cm) eluting with a gradient of 5% acetonitrile/95% water/0.05% TFA to 95% acetonitrile/5% water/0.05% TFA over 15 minutes and then held at 95% acetonitrile/5% water/0.05% TFA for 5 minutes. References to concentration or evaporation of solutions refer to concentration on a rotary evaporator.

Synthesis of (R)-1,1,1-Trifluoro-4-(5-fluoro-2-methoxyphenyl)-4-methyl-2-(1H-pyrrolo[2,3-c]pyridin-2-ylmethyl)pentan-2-ol

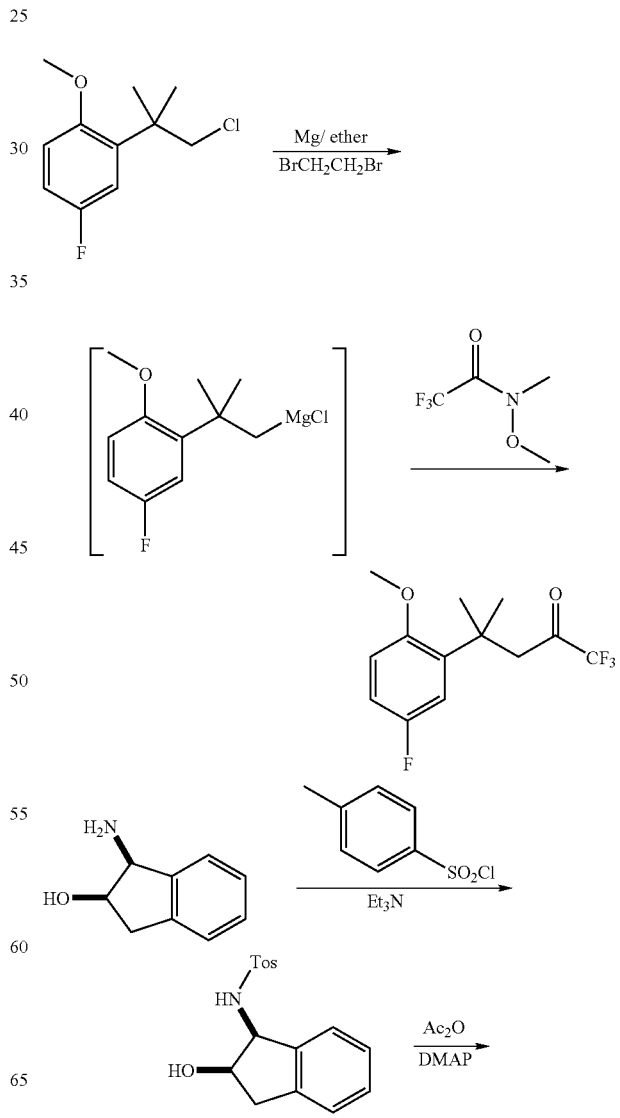

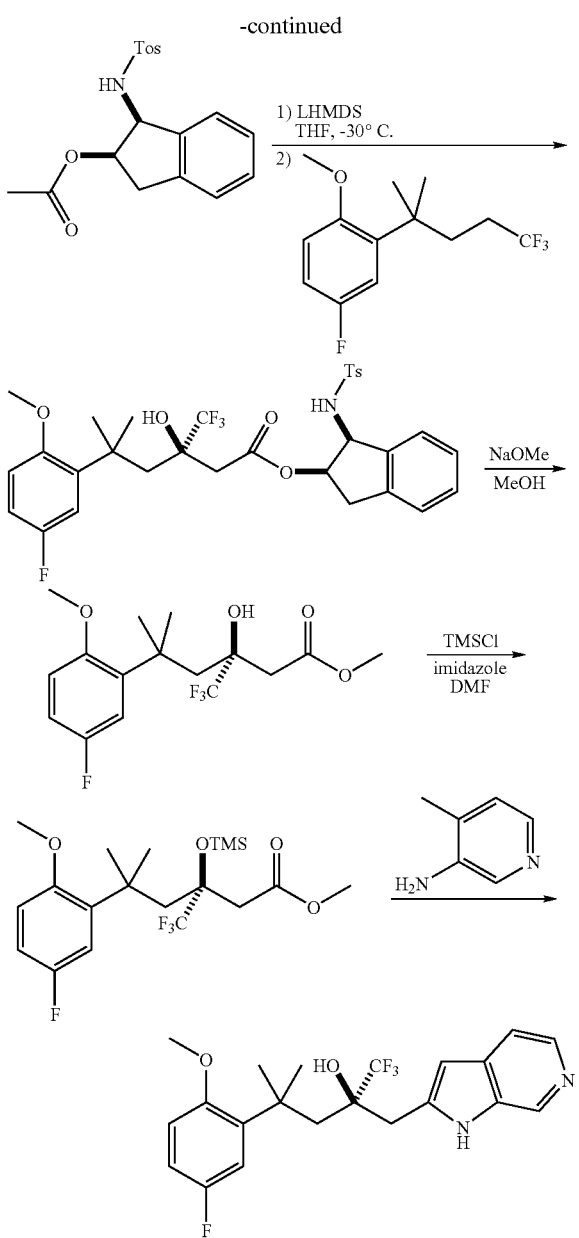

Magnesium turnings were placed in a 5,000 mL three-neck flask equipped with a mechanical stirrer and one addition funnel. The flask was heated to 120° C. under vacuum and then flushed with nitrogen while cooling to ambient temperature. After cooling to ambient (room) temperature, the flask was kept under constant nitrogen flush. Then 1000 mL of anhydrous diethyl ether were added and the mixture was stirred at ~260 rpm. Dibromoethane (87.0 g, 0.46 mol) was loaded in the addition funnel and was added slowly to the flask while the temperature was kept between 22° C.–25° C. with a water bath (note: the addition of dibromoethane to the flask is quite exothermic). When finished (approximately 1.5 hours), the magnesium turned grey. 2-(2–Chloro-1,1-dimethylethyl)-4-fluoro-1-methoxybenzene (100.0 g, 0.46 mole) and 87.0 g (0.46 mole) of dibromoethane dissolved in 1000 mL of anhydrous ether were loaded in the addition funnel and the solution was added to the reaction flask while the temperature was kept between 22° C.–25° C. When finished (approximately 3 hours), the reaction was stirred at room temperature for 15 hours. HPLC analysis indicated that there was no starting chloride left. The solution was stirred at ~350 rpm while cooling to −10° C. 2,2,2-Trifluoro-N-methoxy-N-methylacetamide (72.0 g, 0.46 mole) was then added while the temperature was kept below −5° C. When finished, the slurry was warmed up to room temperature and stirred for 4 hours. 2 N HCl (600 mL, 1.20 mole) and 500 mL of water were added to the slurry while stirring at 300 rpm for 0.5 hour. After the phase separation, the organic layer was washed successively with 500 mL of water, 500 mL of saturated aqueous sodium bicarbonate (NaHCO$_3$), and 500 mL of brine. Filtration and concentration gave 128.2 g (80% yield) of crude 1,1,1-trifluoro-4-(5-fluoro-2-methoxyphenyl)-4-methylpenta-2-one as a slightly yellow liquid that was readily purified by vacuum distillation.

In a 500 mL flask, (1S,2R)-1-amino-2-indanol (22.3 g, 150 mmol) was added at room temperature, followed by 100 mL of anhydrous THF and triethylamine (62.7 mL, 450 mmol). The addition funnel was rinsed with 10 mL of THF. Tosyl chloride (28.6 g, 150 mmol) solution in THF (80 mL) was slowly added in so that the temperature did not exceed 27° C. The addition funnel was rinsed with THF (35 mL). The reaction was stirred at 15° C. for 1 hour and HPLC showed the complete conversion to the desired tosylate.

To the above reaction mixture was added 4-dimethylaminopyridine (DMAP) (0.92 g, 7.5 mmol) solution in THF (15 mL), followed by slow addition of acetic anhydride (17.0 mL, 180 mmol) and a THF rinse (10 mL) over 15 minutes, while maintaining the temperature below 27° C. The reaction was stirred at 15° C. for 1 hour and HPLC showed the complete conversion to the desired acetate ester.

The reaction was quenched with 100 mL of 5% sodium bicarbonate solution (temperature rose to 30° C.) and the mixture was stirred for 40 minutes. The organic layer was diluted with 250 mL of tert-butyl methyl ether (MTBE), washed with two 250 mL portions of 2 N HCl solution, a 125 mL portion of water, a 125 mL portion of 5% sodium bicarbonate solution, and a 125 mL portion of brine. The organic layer was separated and concentrated to about 100 g of a thick oil. Recrystallization from 200 mL of hexane afforded the desired acetic acid (1S,2R)-1-(toluene-4-sulfonylamino)indan-2-yl ester (49 g, 95% yield) as a white solid.

To a stirred solution of the above chiral ester (103.6 g, 0.3 mol) in 200 mL of dry THF was added a 1 M solution of lithium bis(trimethylsilyl)amide (750 mL, 0.75 mol) in THF via cannula, under nitrogen gas at ~30° C. The resulting brown solution was stirred for 30 minutes at −30° C. A solution of 1,1,1-trifluoro-4-(5-fluoro-2-methoxyphenyl)-4-methyl-pentan-2-one (83.47 g, 0.3 mol) in 200 mL of THF was added to this solution slowly while the reaction temperature was maintained at −30° C. The resulting reaction mixture was stirred at −30° C. for 30 minutes, and then was quenched by addition of about 700 mL of 2 M aqueous HCl solution to bring the pH to 7. The organic layer was concentrated under reduced pressure and the residual water was removed by azeotropic distillation of EtOAc to afford the desired crude aldol product. Silica gel chromatography (20% EtOAc/hexane) of crude product afforded a mixture of two diastereomers. Recrystallization (10% EtOAc acetate/hexane) gave the major isomer, (R)-5-(5-fluoro-2-methoxyphenyl)-3-hydroxy-5-methyl-3-trifluoromethylhexanoic acid (1S,2R)-1-(toluene-4-sulfonylamino)indan-2-yl ester (48 g, 25% yield, 98.5% e.e.) as a white solid.

The above recrystallized aldol product (44.0 g, 70.55 mmol) was dissolved in 440 mL of MeOH in a dry flask. 1.0 mL (4.4 mmol) of 25% NaOMe in MeOH solution was then added in one portion. The clear solution was stirred at ambient temperature for 15 hours. HPLC analysis showed that all starting material had been consumed. 10 mL of saturated ammonium chloride (NH$_4$Cl) solution was then added and the pH changed from 13 to 8. The solvent was then removed under vacuum to give a white solid. 200 mL of MTBE and 500 mL of hexane were added and the mixture was stirred for 1 hour at ambient temperature. The solid was filtered off and washed with two 20 mL portions of hexane. The filtrate was washed with 200 mL of 2 N NaOH, 200 mL of saturated ammonium chloride solution, 200 mL of brine, and then dried over magnesium sulfate (MgSO$_4$). The solvent was removed under vacuum to give (R)-3-hydroxy-5-(2-methoxy-5-methylphenyl)-5-methyl-3-trifluoromethyl-hexanoic acid methyl ester (24.6 g, 99% yield) as a colorless oil which solidified slowly.

The above methyl ester (22.6 g, 64.1 mmol) and 10.9 g (160 mmol) imidazole were dissolved in 100 mL of anhydrous DMF and cooled to –10° C. Trimethylsilyl chloride (TMSiCl, 10.5 g) was added over 10 minutes while the internal temperature was kept below –10° C. The solution was allowed to warm up to ambient temperature and was stirred for 60 hours. HPLC analysis showed no starting material was left. 200 mL of hexane and 100 mL of saturated sodium bicarbonate were then added and the mixture was stirred for 10 minutes. The layers were separated and the organic layer was washed with two 100 mL portions of water and a 100 mL portion of brine, and then dried over magnesium sulfate. Solvent was removed under vacuum to yield 26.6 g of the desired trimethylsilyl ether (98% yield) as a colorless oil.

3-Amino-4-picoline (2.16 g, 20.0 mmol) was dissolved in 80 mL of anhydrous THF in a dry flask under a nitrogen blanket. The solution was cooled to –70° C. sec-BuLi (1.4 M, 43 mL, 60.0 mmol) in cyclohexane was added via syringe over 20 minutes. The mixture was then warmed to 21° C. and stirred for 3 hours. After cooling back to –70° C., the above trimethylsilyl ether (2.54 g, 5.8 mmol) in 5 mL of anhydrous THF was added over 20 minutes. The solution darkened and after stirring 20 minutes, the solution was warmed to –40° C. and stirred an additional 20 minutes. The solution was then cooled back to –70° C. 2 N HCl (50 mL) was then added over 15 minutes and the mixture was allowed to warm up to 0° C. and stir for 30 minutes. The bright yellow slurry had a pH of less than 2. 50 mL of 1 N NaOH was then added and the pH was adjusted to greater than 10. 200 mL of MeOH was also added and the mixture was stirred for 1 hour to allow all the intermediates to convert to product. Then 100 mL of saturated ammonium chloride solution was added and the pH was adjusted to 7. The organic solvent was removed under vacuum and 200 mL of MTBE and 100 mL of saturated sodium bicarbonate solution were added. The layers were separated and the organic layer was washed with three 100 mL portions of water and a 100 mL portion of brine and then the organic layer was dried over magnesium sulfate. The solvent was evaporated under vacuum to yield 2.43 g yellow foamy solid, which was crystallized using MTBE to give the title compound (1.28 g, 55% isolated yield).

What is claimed is:

1. A process for stereoselective synthesis of a compound of formula (G)

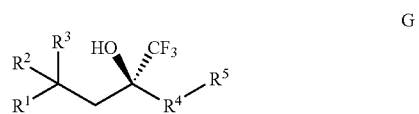

wherein:
R' is an aryl or heteroaryl group, each optionally independently substituted with one to three substituent groups,
wherein each substituent group of R1 is independently C$_1$–C$_5$ alkyl, C$_2$–C$_5$ alkenyl, C$_2$–C$_5$ alkynyl, C$_3$–C$_8$ cycloalkyl, heterocyclyl, aryl, heteroaryl, C$_1$–C$_5$ alkoxy, C$_2$–C$_5$ alkenyloxy, C$_2$–C$_5$ alkynyloxy, aryloxy, C$_1$–C$_5$ alkanoyloxy, C$_1$–C$_5$ alkanoyl, aroyl, trifluoromethyl, trifluoromethoxy, or C$_1$–C$_5$ alkylthio,
wherein each substituent group of R$^1$ is optionally independently substituted with one to three substituent groups selected from methyl, methoxy, fluoro, chloro, or alkoxy;
R$^2$ and R$^3$ are each independently hydrogen or C$_1$–C$_5$ alkyl, or R$^2$ and R$^3$ together with the carbon atom they are commonly attached to form a C$_3$–C$_8$ spiro cycloalkyl ring; R$^4$ is C$_1$–C$_5$ alkyl, C$_2$–C$_5$ alkenyl, or C$_2$–C$_5$ alkynyl, each optionally independently substituted with one to three substituent groups,
wherein each substituent group of R$^4$ is independently C$_1$–C$_3$ alkyl, hydroxy, halogen, amino, or oxo; and
R$^5$ is a heteroaryl group optionally independently substituted with one to three substituent groups,
wherein each substituent group of R$^5$ is independently C$_1$–C$_5$ alkyl, C$_3$–C$_8$ cycloalkyl, C$_1$–C$_5$ alkoxy trifluoromethyl, trifluoromethoxy, trifluoromethylthio, or C 1–C$_5$ alkylthio,
wherein each substituent group of R$^5$ is optionally independently substituted with one to three substituent groups selected from C$_1$–C$_3$ alkyl, C$_1$–C$_3$ alkoxy, or trifluoromethyl,
the process comprising:
(a) reacting a starting material of formula A with a first protecting group agent PG-Y, where Y is a leaving group, in a suitable solvent, followed by addition of an acetylating reagent and a suitable base to prepare a protected intermediate of formula B

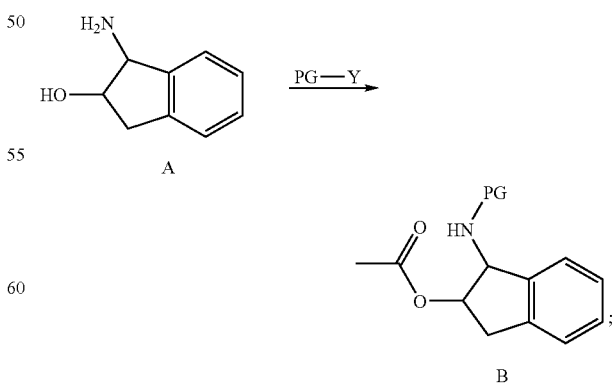

(b) reacting the protected intermediate of formula B with a trifluoromethyl-substituted ketone of formula C in the presence of a suitable base in a suitable solvent to obtain a compound of formula D

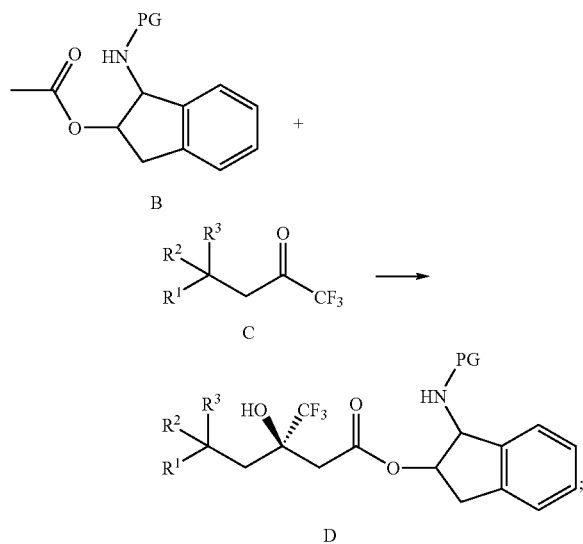

(c) reacting the compound of formula D with a suitable metal alkoxide, $(R^A\text{---}O)_\mu M$, where $R^A$ is an alkyl or aryl group, M is a suitable metal atom, and μ is an integer number, in a suitable solvent followed by reaction of the tertiary alcohol with a second protecting group agent PG'-Y', where Y' is a leaving group, to obtain the ester of formula E

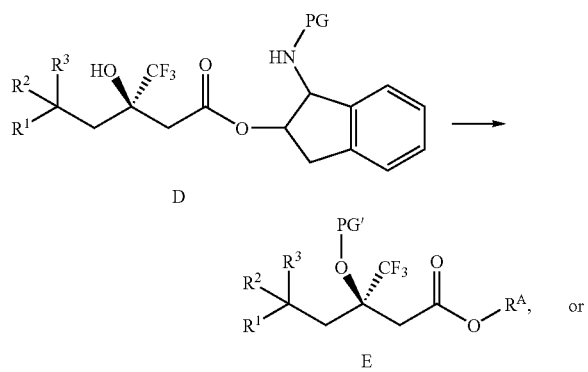

(c') hydrolyzing the compound of formula D followed by esterification of the free acid with a suitable alcohol, $R^B\text{---}OH$, where $R^B$ is an alkyl or aryl group, and protection of the tertiary alcohol as in (c) to provide the ester of formula E

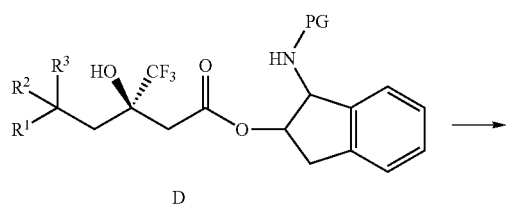

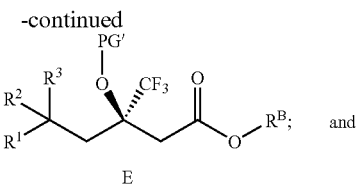

(d) reacting the ester of formula E with the compound of formula F, where one or two of W, X, Y, or Z is N and the remaining are CH optionally substituted on the ring or methyl group with a substituent compatible with alkyl lithium, in the presence of a suitable base, in a suitable solvent to obtain a compound of formula G

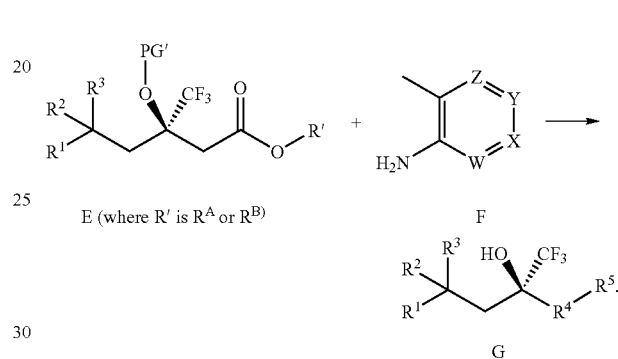

2. The process according to claim 1, wherein the suitable solvent of step (a) is dimethyl ether, diethyl ether, dipropyl ether, diisopropyl ether, dibutyl ether, tetrahydrofuran (THF), ethylene glycol dimethyl ether (DME), tert-butyl methyl ether (MTBE), or a mixture thereof.

3. The process according to claim 1, wherein the suitable base for step (a) is a trialkylamine, a pyridine base, or an inorganic base.

4. The process according to claim 3, wherein the suitable base for step (a) is triethyl amine (TEA), diisopropylethyl amine, pyridine, 4-dimethylaminopyridine (DMAP), $Na_2CO_3$, or NaOH.

5. The process according to claim 1, wherein the first protecting group PG is an aryl or alkyl sulfonyl group and the first leaving group Y is Cl, Br, I, MsO, TsO, or TfO.

6. The process according to claim 1, wherein the suitable acetylating reagent for step (a) is acetic anhydride or acetyl chloride.

7. The process according to claim 1, wherein the suitable solvent of step (b) is diethyl ether, dipropyl ether, diisopropyl ether, dibutyl ether, tetrahydrofuran (THF), ethylene glycol dimethyl ether (DME), tert-butyl methyl ether (MTBE), toluene, hexane, heptane, or a mixture thereof.

8. The process according to claim 1, wherein the suitable base for step (b) is lithium hexamethyldisilazide (LiHMDS), sodium hexamethyldisilazide (NaHMDS), potassium hexamethyldisilazide (KHMDS), LDA, LiH, NaH, KH, trialkylamine/$R_2BOTf$ (dialkylboryl trifluoromethanesulfonate), trialkylamine/$TiCl_4$ or trialkylamine/$TiCl_2(OiPr)_2$, optionally including additives selected from sparteine, $MgBr_2$, $TiCl_4$, and $ZnCl_2$.

9. The process according to claim 1, wherein M of the suitable metal alkoxide of step (c) is lithium, sodium, potassium, rubidium, or cesium, and μ is 1.

10. The process according to claim 1, wherein M of the suitable metal alkoxide of step (c) is magnesium, calcium, or barium, and μ is 2.

11. The process according to claim 1, wherein $R^4$ of the suitable metal alkoxide of step (c) is an alkyl or aryl group.

12. The process according to claim 1, wherein the suitable metal alkoxide of step (c) is an alkali metal alkoxide.

13. The process according to claim 1, wherein the suitable solvent of step (c) is tetrahydrofuran (THF), methanol, ethanol, water, DME, MTBE, isopropyl alcohol (IPA), dimethyl ether, dipropyl ether, diisopropyl ether, or a mixture thereof.

14. The process according to claim 1, wherein the hydrolysis of step (c') is accomplished with an alkali metal hydroxide, phase transfer hydrolysis, or acid hydrolysis in a suitable solvent selected from tetrahydrofuran (THF), methanol, ethanol, water, DME, MTBE, IPA, dimethyl ether, dipropyl ether, diisopropyl ether, or a mixture thereof.

15. The process according to claim 1, wherein the esterification of step (c') is carried out by treatment of the free acid with methanol in the presence of an acid catalyst.

16. The process according to claim 1, wherein the second protecting group PG' is a trialkylsilyl group, lower alkyl ether, lower alkyl group, or internally protected as a β-lactone with the terminal carboxyl group, and the second leaving group Y' is Cl, Br, I, MsO, TsO, and TfO.

17. The process according to claim 1, wherein the suitable solvent of step (d) is THF, DME, diethyl ether, dipropyl ether, diisopropyl ether, dibutyl ether, MTBE, toluene, benzene, xylene, hexane, pentane, heptane, methylene chloride, or a mixture thereof.

18. The process according to claim 1, wherein the suitable base of step (d) is n-BuLi, sec-BuLi, or tert-BuLi, optionally including additives selected from N,N,N',N'-tetramethylethylenediamine (TMEDA), β-dialkylaminoalcohols, sparteine, or polyethers.

19. The process according to claim 1, wherein the compound of formula F is 3-amino-4-picoline, 4-amino-3-picoline, 2-amino-3-picoline, or 3-amino-2-picoline, each optionally substituted on the ring or methyl group with a substituent compatible with alkyl lithium.

* * * * *